United States Patent [19]

Doynow

[11] 4,299,211
[45] Nov. 10, 1981

[54] EXTRACTION SPLINT

[76] Inventor: David Doynow, 31 Sherbrooke Rd., Hartsdale, N.Y. 10530

[21] Appl. No.: 143,424

[22] Filed: Apr. 24, 1980

[51] Int. Cl.³ .............................................. A61F 5/04
[52] U.S. Cl. .................................. 128/89 R; 128/134
[58] Field of Search .................... 128/87 R, 89 R, 75, 128/83, 134, 78

[56] References Cited

U.S. PATENT DOCUMENTS

| | | | |
|---|---|---|---|
| 3,315,671 | 4/1967 | Creelman | 128/134 |
| 3,606,885 | 9/1971 | Lund | 128/134 |
| 3,620,211 | 11/1971 | Goodell et al. | 128/89 R |
| 4,141,368 | 2/1979 | Meyer | 128/134 |
| 4,194,501 | 3/1980 | Watt | 128/75 |

*Primary Examiner*—John D. Yasko
*Attorney, Agent, or Firm*—Pennie & Edmonds

[57] ABSTRACT

An improved extraction splint which is initially substantially flat but is readily formed by manual means to conform to the contortions in which an injured person may be found and is then applied to that person to immobilize injured parts prior to moving the person for transport to a medical facility. The extraction splint is primarily intended as means for immobilizing relative to each other any or all of the head, neck, arms, shoulders, collarbones and spine of an injured person in the same position in which found.

4 Claims, 4 Drawing Figures

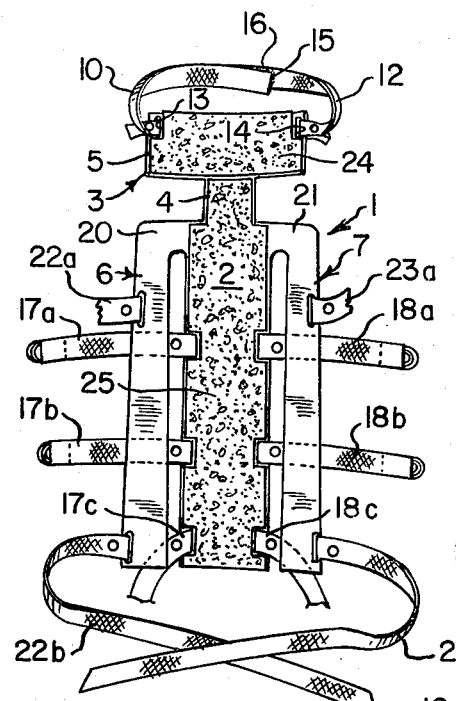
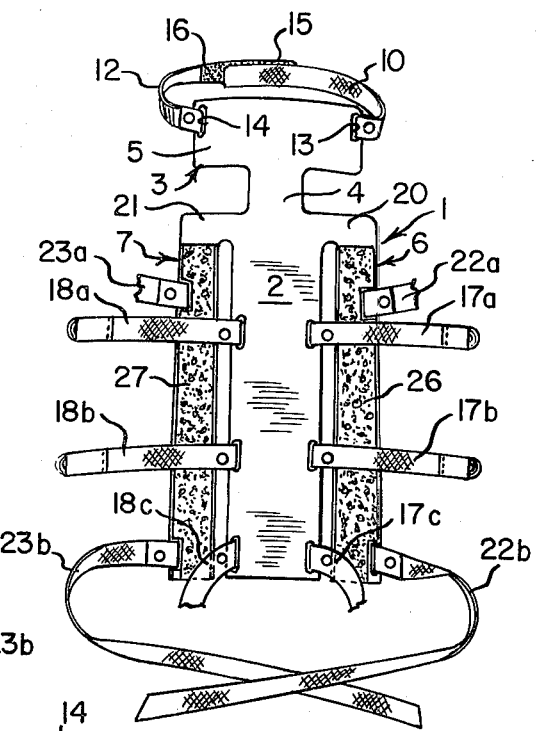
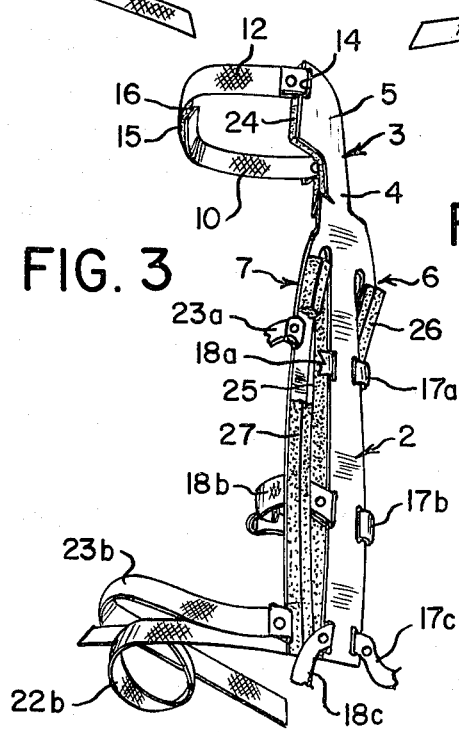
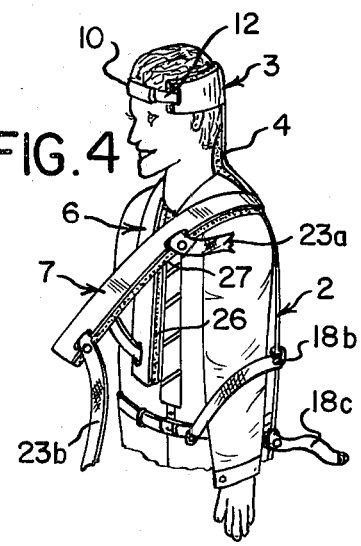

EXTRACTION SPLINT

BACKGROUND OF THE INVENTION

Technical Field

This invention provides an improved extraction splint which is initially substantially flat but is readily formed by manual means to conform to the contortions in which an injured person may be found and is then applied to that person to immobilize injured parts prior to moving the person for transport to a medical facility. The extraction splint of my invention is primarily intended as means for immobilizing relative to each other any or all of the head, neck, arms, collarbones, shoulders and spine of an injured person in the same position in which found, all for the purpose of inhibiting aggravation of an injury already sustained and for preventing further injury due to relative motion of damaged or broken parts of the person's body.

My new extraction splint is also well adapted to immobilization of individual injured extremities such as arms and legs.

Background Art

The most nearly related prior art known to me includes U.S. Pat. No. 3,620,211. The patent describes an extraction splint formed of malleable rods or tubes which are adapted to be formed to the contours of an injured person's vertebral column. It provides only for immobilization of the spine, neck and head of an injured person. My present invention is an improvement thereon in that it combines in a single, compact appliance all the utilitarian features of the patented splint. However, because I have conceived of a substantially different means of constructing the splint, my invention provides a splint which is capable of immobilizing injured shoulders, collarbones and arms relative to the vertebral column and head. It is not uncommon for the bones in one or both of the shoulders and arms to be broken or for the joints thereof to become dislocated in the same accident that breaks bones in the neck and spine or dislocates joints in the vertebral column. Thus, an extraction splint which provides in one appliance the means for quickly and easily immobilizing all of these parts of an injured person is a distinct advantage to emergency personnel whose business it is to get the victim of an accident to a hospital in the shortest possible time without compounding the victim's injuries in the process.

DISCLOSURE OF THE INVENTION

My improved extraction splint comprises a frame formed from pliable material. The frame includes a central portion having a length which approximates the length of the torso of a human. The frame also includes a neck and head brace portion extending longitudinally from one end of the central portion. Finally, the frame includes at least one over-the-shoulder brace portion which is an elongated strip disposed lengthwise of the central portion of the frame. The shoulder brace portion is attached to the central portion adjacent the same end of the central portion as that from which the neck and head brace portion extends.

The extraction splint also comprises a plurality of pliable straps. Individual ones of these straps are engaged respectively with the central, head and shoulder brace portions of the frame. Each strap is sufficiently long such that its reach permits it to clasp the engaged portion of the splint frame to a part of the injured person to be immobilized.

The frame of the splint is initially formed flat so that it may be conveniently stored and carried in an ambulance or other emergency vehicle.

Emergency personnel may quickly examine an accident victim and, upon determining that the victim is injured in such a way that some member or members of the body must be immobilized prior to moving the victim, may manually form the extraction splint to the contours of the victim's body. The splint is then slid into place against the victim's body. Further shaping of the splint may be done if necessary. The victim is then secured to the splint with the pliable straps. The frame material being pliable, the several portions of the frame may be curved either longitudinally or transversely or both as they are being formed to fit the contortions of the victim and secured with the straps. Such curvature of the frame portions tends to stiffen them and enhance their ability to hold the victim in the same contorted position in which he was found. Because the frame is formed of pliable material, it may be manipulated back to a substantially flat condition after use.

The shoulder brace portions of the frame provide a unique function in that either or both of them may be bent out of the plane in which the frame was formed and extended over the shoulder of the victim and then the distal end of the brace may be turned back toward parallelism with the plane of the central portion of the frame. The shoulder restraint provided by this feature of my invention is extremely helpful in some types of injuries. It is particularly valuable where the head or upper vertebral column is the injured part to be restrained, for the brace portions in the over-the-shoulder configuration tend to fix the position of the frame relative to the victim's body and provide enhanced support and restraint when an injury to the head or upper vertebral column requires immobilization of those parts. This feature also facilitates application of the splint to some contortions of an injured person.

BRIEF DESCRIPTION OF THE DRAWINGS

FIG. 1 is a front view of the extraction splint according to the invention;

FIG. 2 is a rear view of the extraction splint shown in FIG. 1;

FIG. 3 is a side view taken from the left side of the extraction splint shown in FIG. 1;

FIG. 4 is a side view taken from the left side showing the extraction splint of FIG. 1 applied with the shoulder brace portions of the splint in the over-the-shoulder configuration.

BEST MODE FOR CARRYING OUT THE INVENTION

An extraction splint according to my invention is useful for both children and adults. However, a well equipped emergency vehicle should have several different sizes of splints to enable emergency personnel to cope most effectively with the variety of injured persons who may be encountered. Thus, where dimensions are prescribed in this specification and the appended claims, it is to be understood that lengths and width specified in terms of the dimensions of a human body are relative to the average dimensions of infants or of children in a given age bracket or of adults of various generalized physiques. In short, a splint according to my invention may be tailored to any one of these groups. In an emergency, however, it is quite possible to effectively immobilize an injured person of a given physique with a splint which was designed for use on persons of somewhat different size.

The principal component of an extraction splint according to the present invention is a frame 1 which is formed from a sheet of material which is sufficiently pliable that it may be manually shaped by emergency personnel at the scene of an accident, but which becomes rigid enough when curved and folded to provide substantial restraint for injured members of an accident victim.

A suitable material is substantially unalloyed aluminum which has been annealed to a condition such that it typically has a tensile strength of about 6800 psi, an elastic modulus of about $9 \times 10^6$ psi and an elongation of about 60%. In addition to its pliability by manual means, sheets of this material on the order of 1/16 inch thick are substantially transparent to X-rays in that part of the electromagnetic spectrum commonly used for medical diagnosis. While pliable metal alloys or even plastics may be used to form the frame of the splint, it is desirable, although not essential to the practice of the invention, that the material selected be relatively transparent to X-rays, for that characteristic enables hospital personnel to commence X-ray diagnosis of an injured person immediately he arrives there and without relaxing the immobilization provided by the splint before the extent of the victim's injuries is determined.

The frame 1 may be simply die cut from a flat sheet of material of the type just described. The frame itself comprises a central portion 2. In a preferred form the central portion has a length which is approximately the length of the torso of a human body and it has a width which is less than the width of a human torso but greater than approximately the width of a human neck.

A neck and head brace portion 3 extends from the upper end of the central portion as seen in FIGS. 1 and 2. The length of brace portion 3 is approximately the length of the neck and head of a human. While the entire neck and head brace portion may be substantially the same width throughout its length, in this preferred embodiment the brace portion 3 is in the shape of a T as shown in FIG. 1 with the stem 4 of the T being approximately the width of the human neck and the cross 5 of the T being somewhat broader. The advantages of this configuration will be described in more detail at a later time.

The frame of the extraction splint also comprises right and left shoulder brace portions 6 and 7, respectively, the lengths which are approximately the same as the central portion of the frame and the widths of which may be approximately the breadth of the human arm. As initially formed, the shoulder brace portions lie in the same plane as the central portion and they extend longitudinally along the respective longitudinal edges of the central portion.

Each shoulder brace portion is made integral with, or otherwise attached to, the central portion 2 of the frame adjacent the end of the central portion 2 from which the neck and head brace 3 extends. In this preferred embodiment each shoulder portion can be said to have the form of an inverted L. The proportions are such that the horizontal distance between the knees of the L-shaped shoulder brace portions 6 and 7 approximates the shoulder span of the human body.

The various portions of the frame are provided with straps which are adapted to clasp each portion of the frame to the body of an injured person. These straps may take various forms. For example, a strap may be riveted directly to a portion of a frame at a suitable location or it may be merely threaded through suitably positioned slots formed in the frame. Suitable fasteners such as buckles or snap fasteners may be used to fasten the free ends of the straps about the various parts of the injured person and thereby secure the person to the frame in an immobilized position. However, I prefer to use straps that are looped at one end through slots formed in the margins of the several brace portions of the splint frame and the loops are closed by any suitable means such as snap fasteners or rivets. This assures that the straps will remain secured to the frame and will not be lost. The distal portions of the straps are provided with hook and loop fastening means which make the straps readily adjustable to any required length within their overall lengths. Hook and loop fasteners are widely marketed commercially under the trademark "VELCRO" and straps made with the hook and loop fastening means woven in as an integral part thereof are marketed commercially under the trademark "VELSTRAP".

Typically, straps may be provided as shown in FIGS. 1, 2 and 3. Head straps 10 and 12 are shown with their inner ends looped through slots 13 and 14, respectively, in the margins of the cross of the T-shaped neck and head brace. The distal ends of these straps are shown secured together by the hook and loop fasteners 15 and 16.

Straps for securing the torso of an injured person to the central portion 2 of the splint are shown at 17a, b, and c and at 18a, b and c. Similarly, straps for the shoulder brace portions 20 and 21 are shown at 22a and b and at 23a and b. The number and placement of straps shown in the Figures are illustrative only. Different numbers of straps and other placements of them may be used.

To make the splint as comfortable as possible for an injured person some or all of the flat areas of the frame may be covered with cushioning material such as textile padding or sheeted foam rubber or plastic. Typical locations for such cushioning are shown at 24 on the neck and head brace 3, at 25 on the front of the central portion 2 and at 26 and 27 on the back sides of the shoulder brace portions.

Certain portions of the frame may be made more rigid by pressing corrugations into the frame material. For example, the stem of the T-shaped neck and head brace 3 could be made more rigid and inflexible by corrugations parallel to its length. The same technique may be used at other places on the frame if desired.

The extraction splint of my invention may be manually formed and applied to an injured person in virtually any contorted position in which he may be found. The technique for forming and applying the splint will be described in connection with a specific example which is illustrated in FIG. 4. There the splint is shown as it would be applied to a person whose injuries require immobilization of the neck and upper vertebral column and the shoulders.

The central portion 2 of the splint is curved transversely and longitudinally to the approximate contours of the victim's back. The shoulder brace portions 6 and 7 are then bent forward so that they extend out of the plane of the splint. The splint is placed on the victim with the central portion 2 against the victim's back and the shoulder brace portions extending forwardly over the victim's shoulders. At this time the central portion of the splint may be secured in place with straps 17a, b, c and 18a, b, c.

Now the shoulder brace portions may be bent down against the front of the victim's torso. In FIG. 4 the shoulder brace portion 6 is shown after it has been formed in place against the torso, while the other shoulder brace portion 7 is shown extending over the victim's left shoulder, but before it has been bent into place against the torso. After both shoulder brace portions have been bent into place they may be secured in place with straps 22a, b and 23a, b in cooperation with the lowermost straps 17c and 18c on the central portion of the splint or with each other.

In this configuration the central and shoulder brace portions of the splint restrain the shoulders with respect to the torso and immobilize the upper vertebral column. Now the neck and head may be immobilized by means of the T-shaped neck and head brace 3, the cross piece of which is formed about the back and sides of the victim's head. The neck and head are then immobilized by means of straps 10 and 12.

Of course, the sequence in which the various parts of the splint are formed and applied to the victim may be different in particular circumstances. Moreover, the splint may be applied in different ways to immobilize other injured members. For example, one or both of the shoulder brace portions could as well have been used as splints for broken arms. In other circumstances the splint could be used to immobilize a broken leg by curving the central portion into a U-shaped channel, laying the leg in the channel and strapping it in place with straps 17a, b, c and 18a, b, c.

I claim:

1. An improved extraction splint capable of immobilizing the head, shoulders and vertebral column of an injured person, which splint comprises
   (a) a frame formed from pliable material, said frame comprising
      1. a central portion having a length which approximates the length of a human torso;
      2. a neck and head brace portion which extends longitudinally from one end of said central portion;
      3. and at least one over-the-shoulder brace portion which is an elongated strip disposed lengthwise of said central portion and which is attached at one end to the central portion adjacent that end of the central portion from which the neck and head brace portion extends;
      4. wherein the several portions of said frame may be manually deformed to accommodate the splint to the contortions in which an injured person may be found;
   (b) and a plurality of straps, individual ones of said straps being engaged respectively with said central, neck and head brace portion and said shoulder brace portions, each of said straps having a reach sufficient to clasp the engaged portion of the frame to a part of the body of an injured person.

2. An improved extraction splint according to claim 1 in which said central portion has a width which is less than the width of a human torso but greater than the width of the human neck, and is provided with right and left shoulder brace portions disposed lengthwise adjacent the respective longitudinal edge of said central portion and attached thereto adjacent that end of the central portion from which the neck and head brace portion extends.

3. An improved extraction splint according to either of claims 1 or 2 and in which the several portions of said frame are formed unitarily from a sheet of metallurgically soft metal which is substantially transparent to X-rays.

4. An improved extraction splint capable of immobilizing the head, shoulders and vertebral column relative to the torso of an injured person, which splint comprises
   (a) a unitary frame formed from a sheet of metallurgically soft, pliable metal which is substantially transparent to X-rays, said frame comprising;
      (1) a substantially rectangular central portion having a length which approximates the length of the torso of a human and having a width which is less than the width of the torso but greater than the width of the neck of a human;
      (2) a T-shaped neck and head brace portion with the stem of the T extending longitudinally from one end of said central portion for a distance which approximates the length of a human neck and head and the cross of the T extending substantially parallel to the end of said central portion;
      (3) right and left shoulder brace portions, each of which is substantially L-shaped with the stem of the L disposed lengthwise adjacent the respective longitudinal edge of said central portion and the distal end of the foot of the L joined to said central portion adjacent that end of the central portion from which said neck and head brace extends, wherein the several portions of said frame may be manually deformed from the initial flat form to accommodate the splint to the contortions in which an injured person may be found; and
   (b) at least one pair of straps for each of said central, neck and head and shoulder brace portions, respectively, one end of each such straps being fixed to the respective portion, and fastening means for each pair of straps for securing the distal ends of the straps together, the reach of each pair of straps being sufficient to clasp that portion of the frame to a part of the body of an injured person.

* * * * *